United States Patent [19]

Kobayashi et al.

[11] Patent Number: 5,723,633
[45] Date of Patent: Mar. 3, 1998

[54] PYRAN DERIVATIVE, PHOTOSENSITIVE RESIN COMPOSITION, AND HOLOGRAM RECORDING MEDIUM USING IT

[75] Inventors: Shin Kobayashi, Atsugi; Susumu Matsumura, Kawaguchi; Naosato Taniguchi, Machida; Yoko Yoshinaga; Toshiyuki Sudo, both of Kawasaki; Hideki Morishima, Tokyo; Tadashi Kaneko, Isehara, all of Japan

[73] Assignee: Canon Kabushiki Kaisha, Tokyo, Japan

[21] Appl. No.: 575,387

[22] Filed: Dec. 20, 1995

Related U.S. Application Data

[62] Division of Ser. No. 248,093, May 24, 1994, Pat. No. 5,492,942.

[30] Foreign Application Priority Data

May 25, 1993 [JP] Japan .................. 5-144423

[51] Int. Cl.$^6$ .................. C07D 315/00; C07D 209/04; C07D 455/06
[52] U.S. Cl. .................. 549/426; 549/425; 548/491; 546/93; 546/95; 546/166; 540/586; 540/593
[58] Field of Search .................. 549/425, 426; 548/491; 546/93, 95, 166; 540/586, 593

[56] References Cited

U.S. PATENT DOCUMENTS

| | | | |
|---|---|---|---|
| 3,380,831 | 4/1968 | Cohen et al. | 96/115 |
| 3,852,683 | 12/1974 | Webster et al. | 331/94.5 L |
| 4,146,707 | 3/1979 | Van Allen et al. | 542/433 |
| 4,287,277 | 9/1981 | Matsumoto et al. | 522/113 |
| 4,769,292 | 9/1988 | Tang et al. | 428/690 |
| 5,418,113 | 5/1995 | Yoshinaga et al. | 522/28 |
| 5,422,204 | 6/1995 | Yoshinaga et al. | 522/25 |

FOREIGN PATENT DOCUMENTS

| | | |
|---|---|---|
| 0281381 | 9/1988 | European Pat. Off. . |
| 2156723 | 6/1973 | France . |
| 2002528 | 2/1979 | United Kingdom . |
| WO86-06374 | 11/1986 | WIPO . |

OTHER PUBLICATIONS

Chemical Abstracts, vol. 116, No. 18, 1992, Columbus, Ohio, US; Abstract No. 176114t, p. 96, *abstract* & DD-A-296 801 (T.U. Dresden).

Chemical Abstracts, vol. 117, No. 4, 1992, Columbus, Ohio, US; Abstract No. 176; *abstract* & JP-A-0414 083 (Fujitsu) 20 Jan. 1992.

Hammond, "LASER ... ", Optics. Comm. vol. 29, No. 3, pp. 331-333, Jun. 1979.

*Primary Examiner*—Amelia Averill Owens
*Attorney, Agent, or Firm*—Fitzpatrick, Cella, Harper & Scinto

[57] ABSTRACT

A pyran derivative has a structure of $$R^2R^3C=(C_5H_2R^1O)-(CH=CH)_n-C_6H_2R^6R^7-NR^4R^5$$

wherein n is 3 or 4; $R^1$ is a proton, alkyl or phenyl group; each of $R^2$ and $R^3$ is independently a cyano, alkoxycarbonyl having an alkyl, acyl having an alkyl, aracyl having phenyl, sulfonyl, aryl, or aryloxy; each of $R^4$ and $R^5$ is an alkyl group; and each of $R^6$ and $R^7$ is a proton, provided that $R^4$ and $R^5$ are alkyl groups, and a pair of $R^4$ and $R^6$ as well as a pair of $R^5$ and $R^7$ can be bonded to each other to form a heterocycle.

A photosensitive composition comprises a polymerizable compound, a polymerization initiator and a photosensitizer which is the pyran derivative. A photosensitive resin composition comprises a crosslinkable polymer, a crosslinking agent and the photosensitizer. A hologram recording medium mainly comprises the photosensitive composition or the photosensitive resin composition.

2 Claims, 6 Drawing Sheets

PYRAN DERIVATIVE, PHOTOSENSITIVE RESIN COMPOSITION, AND HOLOGRAM RECORDING MEDIUM USING IT

This application is a division of application Ser. No. 08/248,093 filed May 24, 1994, now U.S. Pat. No. 5,492,942.

BACKGROUND OF THE INVENTION

1. Field of the Invention

The present invention relates to a novel pyran derivative, and more specifically, it relates to a novel pyran derivative which has sensitivity to light in a visible light range, particularly in a wavelength range longer than green light and which can function as a photosensitizer for a photopolymerizable or photocrosslinkable photosensitive resin composition.

Furthermore, the present invention relates to a photopolymerizable and/or photocrosslinkable photosensitive resin composition which can be sensitized by the above-mentioned pyran derivative, and a hologram medium in which this composition is used.

2. Related Background Art

In recent years, with the development of dye lasers, various novel compounds have been synthesized as laser dyes. Above all, 4H-pyrans can emit light very efficiently in a wide range of 600 to 700 nm by laser excitation, and therefore they have been developed as dyes for a long-wavelength light zone dye laser (U.S. Pat. No. 3,852,683). Thus, it is expected that these dyes are applied to an EL display utilizing their characteristics by which light is absorbed and fluorescence is emitted (U.S. Pat. No. 4,769,292).

With regard to the application of these dyes to photosensitive materials for electrophotography, various investigations have been made, but they have not been applied as sensitizers by which an electron or energy is transferred to another compound.

Heretofore, among the 4H-pyrans, a compound represented by the formula (7) has been commercially available:

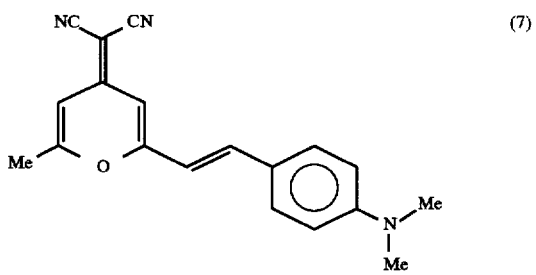

(7)

The above-mentioned compound has an absorption maximum at 481 nm in a dimethyl sulfoxide solution [Optics Comm., 29, p. 331 (1979)], and it has sensitivity to light having a wavelength of 488 nm from an Ar laser but its sensitivity to light having a wavelength of 514.5 nm is poor. In addition, this compound scarcely exhibits the sensitivity to light having a wavelength of 632.8 nm from an He—Ne laser inconveniently. That is, in order to use the 4H-pyrans as the sensitizers for the light having long wavelengths, its absorption maximum is required to be shifted to a longer wavelength side, and it can be considered that a contrivance such as the alteration of substituents is necessary.

SUMMARY OF THE INVENTION

Therefore, the present invention intends to solve the problems of the above-mentioned conventional techniques, and an object of the present invention is to provide a novel pyran derivative having a high absorption sensitivity to light having a wavelength of 514.5 nm from an Ar laser and even to light having a long wavelength of about 632.8 nm from an He—Ne laser.

Another object of the present invention is to provide a photosensitizer comprising the pyran derivative and the like.

Still another object of the present invention is to provide an excellent photopolymerizable and/or photocrosslinkable photosensitive resin composition in which the above-mentioned photosensitizer is used as a photosensitizer for a polymerization initiator and/or a crosslinking agent.

A further object of the present invention is to provide a hologram recording medium having excellent characteristics which mainly comprises this composition.

The above-mentioned objects can be achieved by the present invention.

According to an aspect of the present invention, there is provided a pyran derivative which is characterized by having a structure represented by the following formula (1):

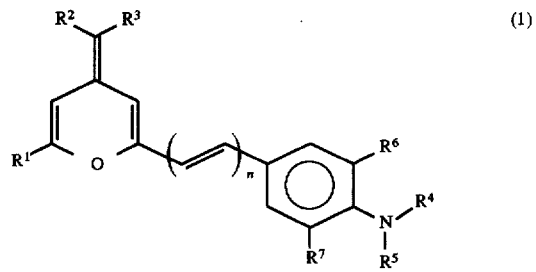

(1)

wherein n is 3 or 4; $R^1$ is a proton, an alkyl group having 1 to 4 carbon atoms, or a substituted or unsubstituted phenyl group; each of $R^2$ and $R^3$ is independently a cyano group, an alkoxycarbonyl group having an alkyl moiety of 1 to 4 carbon atoms, an acyl group having an alkyl moiety of 1 to 4 carbon atoms, an aracyl group having a substituted or unsubstituted phenyl group, a sulfonyl group which is unsubstituted or substituted by an alkyl group having 1 to 4 carbon atoms, a substituted or unsubstituted aryl group, or a substituted or unsubstituted aryloxy group; each of $R^4$ and $R^5$ is an alkyl group having 1 to 6 carbon atoms; and each of $R^6$ and $R^7$ is a proton, provided that $R^4$ and $R^5$ are alkyl groups, and a pair of $R^4$ and $R^6$ as well as a pair of $R^5$ and $R^7$ can be bonded to each other to form a heterocycle such as a five-membered ring, a six-membered ring or a seven-membered ring (e.g., a julolidyl group).

According to another aspect of the present invention, there is provided a photosensitive resin composition comprising a polymerizable compound, a polymerization initiator and a photosensitizer in which a photosensitizer having the structure represented by the following formula (4) is used:

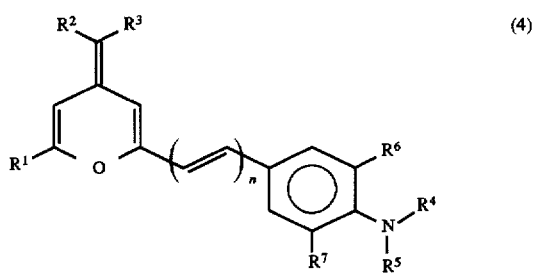

(4)

wherein n is 1 to 4; $R^1$ is a proton, an alkyl group having 1 to 4 carbon atoms, or a substituted or unsubstituted phenyl group; each of $R^2$ and $R^3$ is independently a cyano group, an alkoxycarbonyl group having an alkyl moiety of 1 to 4 carbon atoms, an acyl group having an alkyl moiety of 1 to 4 carbon atoms, an aracyl group having a substituted or unsubstituted phenyl group, a sulfonyl group which is unsubstituted or substituted by an alkyl group having 1 to 4 carbon atoms, a substituted or unsubstituted aryl group, or a substituted or unsubstituted aryloxy group; each of $R^4$ and $R^5$ is an alkyl group having 1 to 6 carbon atoms; and each of $R^6$ and $R^7$ is a proton, provided that $R^4$ and $R^5$ are alkyl groups, and a pair of $R^4$ and $R^6$ as well as a pair of $R^5$ and $R^7$ can be bonded to each other to form a heterocycle such as a five-membered ring, a six-membered ring or a seven-membered ring.

According to another aspect of the present invention, there is provided a photosensitive resin composition comprising a crosslinkable polymer, a crosslinking agent and a photosensitizer in which the photosensitizer having the structure represented by the above-mentioned formula (4) is used.

According to further aspect of the present invention, there is provided hologram recording mediums which mainly comprise the photosensitive resin compositions described above, respectively.

DETAILED DESCRIPTION OF THE PREFERRED EMBODIMENTS

Figure 1:
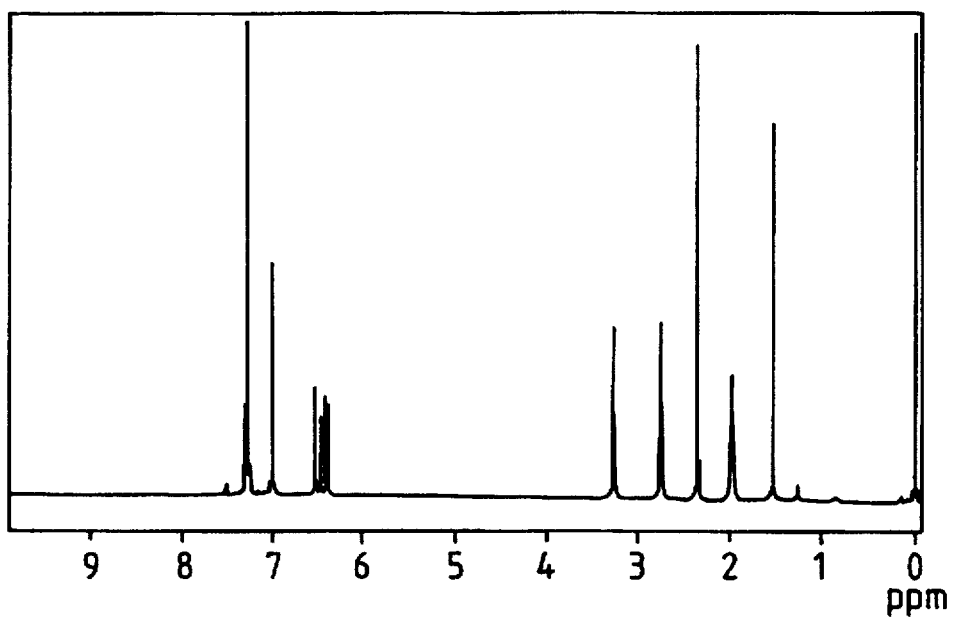
FIG. 1 shows a $^1$H-NMR spectrum of a compound obtained in Example 1.

The present inventors have conducted intensive research to solve the problems of the above-mentioned conventional techniques, and as a result, it has been found that the absorption maximum of a pyran derivative can be shifted to longer wavelength side by using one or both of a technique of changing the amino group moiety of a pyran derivative to a julolidine structure and another technique of increasing the number of double bonds and the thus treated pyran derivative has an excellent photosensitization. In consequence, the present invention has now been attained on the basis of these discoveries.

In general, with regard to cyanine dyes and the like, it has been understood that the number of double bonds of each cyanine is increased in order to shift the absorption maximum of the cyanine to the longer wavelength side. However, with regard to pyran derivatives, such a technique has not been applied so far, though attempts have been made to shift the absorption maximum of a coumarin to the longer wavelength side.

Furthermore, as the synthetic process of an aldehyde represented by the following formula (8) having double bonds which is a precursor of 4H-pyran, in the case of the synthesis of a compound having no amino group, there are known various synthetic methods. However, in the case of the synthesis of a compound having the amino group, the reaction changes owing to the presence of the amino group, and thus some improvement or the like of a synthetic route or a synthetic procedure has been required. Among the pyran derivatives, the synthesis of the derivative having $n \geq 3$ has not been carried out so far, and accordingly, the pyran derivative of the present invention is a novel compound:

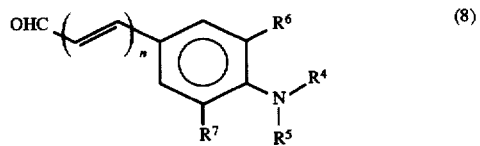

Next, the present invention will be described in more detail with reference to preferred embodiments.

A photosensitizer comprising a pyran derivative of the present invention and a specific pyran derivative can be used as a photosensitizer for various polymerization initiators and/or crosslinking agents. Typical examples of these polymerization initiators and crosslinking agents include diarylhalonium salt derivatives, triazine derivatives, bisimidazole derivatives, halogen compounds and peroxides which can be sensitized by a conventional coumarin dye.

Its sensitization mechanism can be considered to be due to the transfer of an electron or energy from a triplet or a singlet state which can be presumed in the usual coumarin compound, because the polymerization initiator and/or the crosslinking agent to be sensitized is an electron-acceptor.

A photopolymerizable photosensitive resin composition of the present invention can be formed by adding the polymerization initiator or the crosslinking agent and a polymerizable monomer, or a polymer having a crosslinkable portions, and further if necessary, another polymer is added as a binder, to the photosensitizer comprising a pyran derivative of the present invention and a specific pyran derivative.

An organic solvent, an activation assistant and/or a plasticizer and the like can be suitably added to this resin composition system as needed, and the composition system can also be used as a photo resist or the like in various uses.

In particular, the photosensitive resin composition, which is a system comprising the pyran derivative, the polymerization initiator and a monomer mainly comprising carbazole, a system formed by adding a binder polymer to the system, a system comprising the pyran derivative, the crosslinking agent and a crosslinkable polymer mainly comprising carbazole, or a system formed by adding the binder polymer to the system, can be preferably used as a volume phase hologram recording medium.

In this case, the concentration of the pyran derivative can be adjusted in compliance with the film thickness of the volume phase hologram recording medium and an exposure wavelength, and the amount of the pyran derivative is determined in the range of $10^{-3}$ to 1 wt %, preferably $10^{-2}$ to $10^{-1}$ wt % based on the weight of the photosensitive resin composition.

Preferably usable examples of the polymerization initiator and/or the crosslinking agent which can be used in this case include a diarylhalonium salt derivative, a halomethyl-s-triazine derivative, a bisimidazole derivative, a halogen compound and an organic peroxide shown below.

Diarylhalonium Salt Derivative

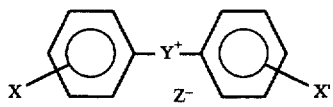 (9)

wherein

X=an alkyl group or a halogen atom,

Y=I, Br or Cl,

Z=PF$_6$, CF$_3$COO, ClO$_4$, SbF$_6$ or AsF$_6$.

Halomethyl-s-triazine Derivative

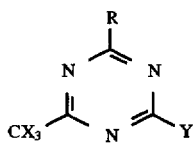 (10)

wherein

X=a halogen atom, preferably a chlorine atom,

Y=CH$_3$, NH$_2$, NHR OR, SR, an alkyl group or an aryl group,

R=a trihalomethyl group, an alkyl group or an aryl group.

Bisimidazole Derivative

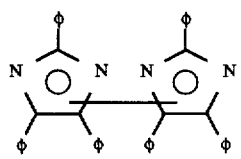 (11)

wherein

φ=an aryl group.

Halogen Compound

CI$_4$, CHI$_3$, CBrCl$_3$ or the like

Peroxide

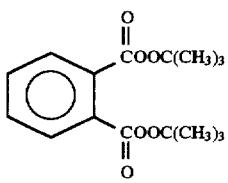 (12)

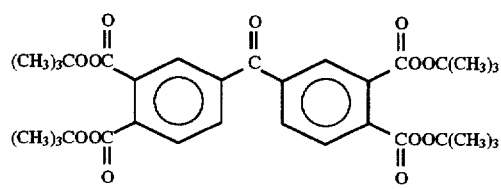 (13)

The polymerization initiator and/or the crosslinking agent is used preferably in an amount in the range of $10^{-2}$ to 10 wt %, more preferably $10^{-1}$ to 10 wt % based on the weight of the photosensitive resin composition of the present invention.

The polymerizable compound which can be used in the photosensitive resin composition of the present invention is a compound containing at least one double bond, and examples of such a compound include monomers, prepolymers such as dimers and oligomers, and mixtures thereof.

Typical examples of the polymerizable compound include 1,5-pentanediol diacrylate, ethylene glycol diacrylate, 1,4-butanediol diacrylate, diethylene glycol diacrylate, hexamethylene glycol diacrylate, 1,3-propanediol diacrylate, decamethylene glycol diarylate, decamethylene glycol dimethacrylate, 1,4-cyclohexanediol diacrylate, 2,2-dimethylolpropane diacrylate, glycerol diacrylate, tripropylene glycol diacrylate, glycerol triacrylate, trimethylolpropane triacrylate, pentaerythritol triacrylate, polyoxy ethylate trimethylolpropane triacrylate and trimethacrylate, the same compounds as mentioned in U.S. Pat. No. 3,380,831, pentaerythritol tetraacrylate, pentaerythritol tetramethacrylate, triethylene glycol dimethacrylate, polyoxypropyltrimethylolpropane triacrylate (462), ethylene glycol dimethacrylate, butylene glycol dimethacrylate, 1,3-propanediol dimethacrylate, 1,2,4-butanetriol trimethacrylate, 2,2,4-trimethyl-1,3-pentanediol dimethacrylate, pentaerythritol trimethacrylate, pentaerythritol tetramethacrylate, 1,5-pentanediol dimethacrylate and diallyl fumarate.

Further examples of the polymerizable compounds include styrene, 2-chlorostyrene, phenyl acrylate, 2-phenylethyl acrylate, 2,2-di(p-hydroxyphenyl)propane diacrylate and methacrylate, 1,4-benzene diacrylate and methacrylate, 1,4-diisopropenylbenzene and 1,3,5-triisopropenylbenzene. However, the radical polymerizable monomers which can be used in the present invention are not limited to the above-mentioned monomers.

In addition, the following spiroorthoesters, spiroorthocarbonates and bicycloorthoesters are also useful as the polymerizable monomers. Particularly, these compounds scarcely contract at the time of the polymerization, and on this account, they can be used as photoresist materials and the like having excellent dimensional accuracy:

 (14)

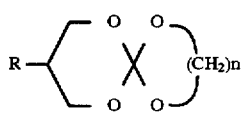 (15)

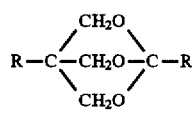 (16)

wherein n is 1 to 5, and

R is an alkyl group or an alkoxy group.

Furthermore, as the polymerizable monomers which can be used in the present invention, there can also be used amphoteric compounds having a structure capable of performing cationic polymerization with an ethylenic unsaturated bond in each molecular structure.

Examples of these amphoteric compounds include vinyl monomers having a carbazole ring (capable of performing the cationic polymerization), for example, N-vinylcarbazole, 3-chlorovinylcarbazole and 3,6-dibromo-9-vinylcarbazole.

In addition, a compound of the following structure having an epoxy ring and an ethylenic unsaturated bond can also be used:

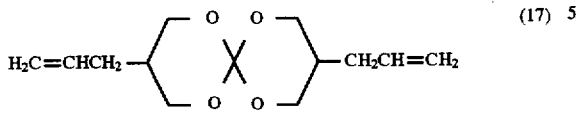

Typical examples of a polymer which is the main component of the photocrosslinkable photosensitive resin composition of the present invention include polyvinylcarbazole, poly-3-chlorovinylcarbazole, poly3-bromovinylcarbazole, poly-3-iodovinylcarbazole, poly- 3-methylvinylcarbazole, poly-3-ethylvinylcarbazole, chlorinated polyvinylcarbazole and brominated polyvinylcarbazole. Other examples of the above-mentioned photocrosslinkable polymer include polystyrenes having a halogen (—Cl, —Br or —I), an amino group, a dimethylamino group and a methoxy group at the p-position, poly(N-vinylindole), poly(N-vinylpyrrole), poly (N-vinylphenothiazine), poly(isopropenylphenol) and poly [4-(N,N-diphenylamino)-phenylmethyl methacrylate].

The above-mentioned vinylcarbazole polymer, if necessary, may be copolymerized with another monomer or blend-polymerized with another polymer in order to control characteristics such as strength and flexibility of, e.g., films obtained therefrom.

For example, the above-mentioned vinylcarbazole may be copolymerized or blend-polymerized with an olefin, a vinyl ester such as vinyl acetate, an ester of acrylic acid or methacrylic acid such as methyl methacrylate, styrene or acrylonitrile.

The vinylcarbazole polymer, when used, can be blended with another polymer such as polystyrene, styrene-butadiene copolymer, styrene-hydrogenated butadiene copolymer, a polycarbonate, a polyacrylate, polyvinylbutyral or polyvinyl acetate. A ratio of the monomer or the copolymer to be added can be optionally selected so as to obtain the desired characteristics.

Next, the present invention will be described with reference to examples and comparative examples.

The scope of the present invention should not be limited to these examples.

EXAMPLE 1

Synthesis of 4,4-Dicyano-6-methyl-julolidyl-4H-pyran (Pyran-J-D1)

2.01 g (0.0100 mol) julolidinal, 1.72 g (0.0100 mol) 4,4-dicyanomethylene-2,6-dimethyl-4H-pyran, 1.09 g (0.0126 mol) piperidine were added in 2.6 cm³ ethanol, and the solution was heated at 75° C. for 2 hours. The precipitation was separated from the solution, and red crystals recrystallized from a chloroform-methanol solution.

The obtained compound was identified by ¹H-NMR, and a spectrum shown in FIG. 1 was obtained, and therefrom the results shown in Table 1 were obtained. In consequence, it was confirmed that the obtained compound had the following structure:

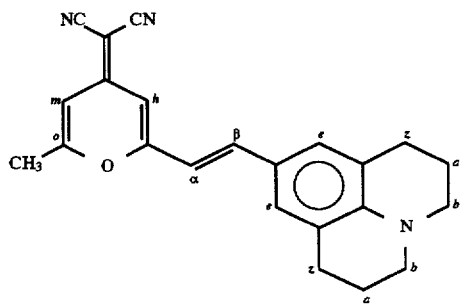

TABLE 1

Measured Results of NMR (pyran-J-D1)

| Chemical Shift (ppm) | Position | Integral Ratio | Multiplicity | J Value (Hz) |
|---|---|---|---|---|
| 2.76 | z | 4H | t | 6 |
| 1.97 | a | 4H | m | 6 |
| 3.26 | b | 4H | t | 6 |
| 7.00 | e | 2H | s | |
| 6.47 | h | 1H | s | |
| 6.54 | m | 1H | s | |
| 2.36 | o | 3H | s | |
| 7.28 | α | 1H | d | 16 |
| 6.39 | β | 1H | d | 16 |

EXAMPLE 2

Figure 2:
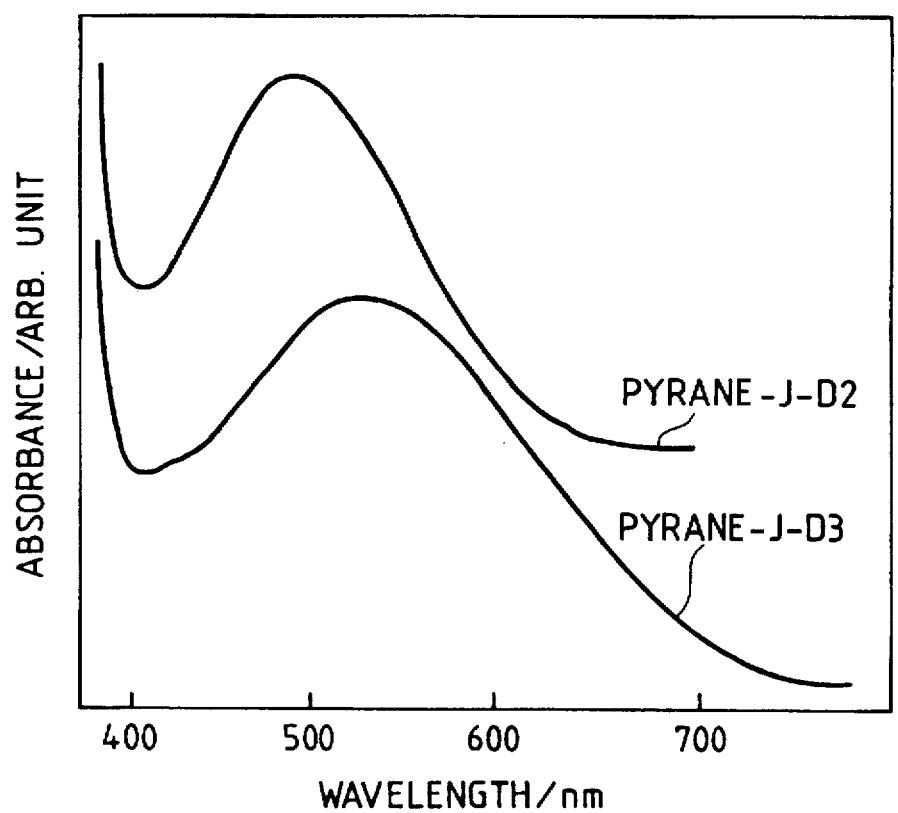
FIG. 2 shows visible light absorption spectra of THF solutions of pyran derivatives obtained in Examples 2 and 4.

The same procedure as in Example 1 was carried out to obtain the following dye (pyran-J-D2). The obtained compound was identified by ¹H-NMR, and the results in Table 2 were obtained. An absorption spectrum of a THF solution of the obtained dye is shown in FIG. 2.

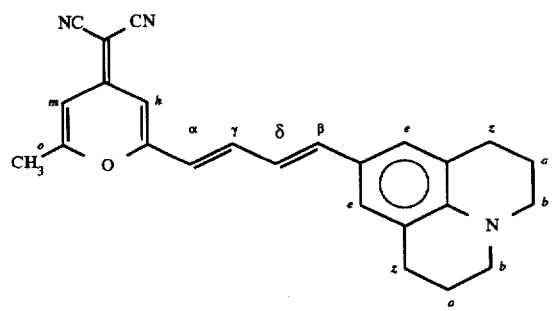

TABLE 2

Measured Results of NMR (pyran-J-D2)

| Chemical Shift (ppm) | Position | Integral Ratio | Multiplicity | J Value (Hz) |
|---|---|---|---|---|
| 2.74 | z | 4H | t | 6 |
| 1.98 | a | 4H | m | 6 |
| 3.23 | b | 4H | t | 6 |
| 6.98 | e | 2H | s | |
| 6.47 | h | 1H | s | |
| 6.54 | m | 1H | s | |
| 2.33 | o | 3H | s | |
| 6.79 | α | 1H | d | 16 |
| 6.10 | β | 1H | d | 16 |

TABLE 2-continued

Measured Results of NMR (pyran-J-D2)

| Chemical Shift (ppm) | Position | Integral Ratio | Multi-plicity | J Value (Hz) |
|---|---|---|---|---|
| 6.68 | γ | 1H | dd | 11, 15 |
| 7.21 | δ | 1H | dd | 11, 15 |

EXAMPLE 3

Figure 3:
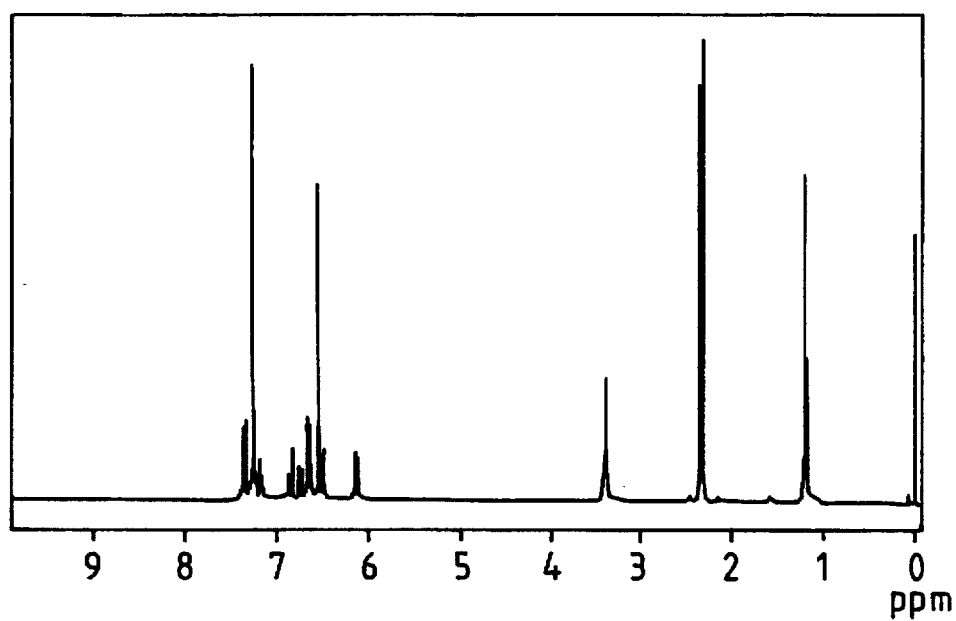
FIG. 3 shows a $^1$H-NMR spectrum of a compound obtained in Example 3.
Figure 4:
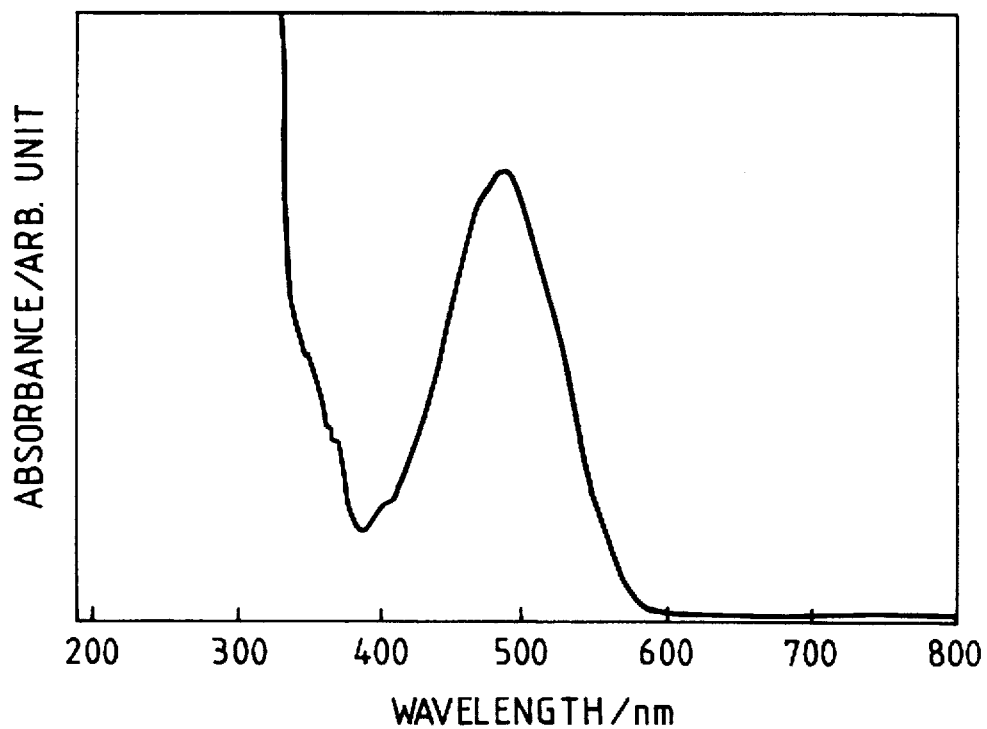
FIG. 4 shows a visible light absorption spectrum of a THF solution of a compound obtained in Example 3.

The same procedure as in Example 1 was carried out to obtain the following dye (pyran-E-D2). The obtained compound was identified by $^1$H-NMR, and a spectrum shown in FIG. 3 was obtained, and therefrom the results in Table 3 were obtained. In consequence, it was confirmed that the obtained compound had the following structure. Furthermore, an absorption spectrum of a THF solution of the obtained dye is shown in FIG. 4.

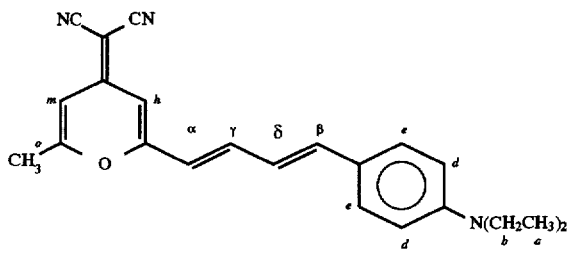

TABLE 3

Measured Results of NMR (pyran-E-D2)

| Chemical Shift (ppm) | Position | Integral Ratio | Multi-plicity | J Value (Hz) |
|---|---|---|---|---|
| 1.20 | a | 6H | t | 7 |
| 3.40 | b | 4H | q | 7 |
| 6.64, 7.35 | d, e | 4H | dd | 9 |
| 6.47 | h | 1H | s | |
| 6.53 | m | 1H | s | |
| 2.32 | o | 3H | s | |
| 6.85 | α | 1H | d | 15 |
| 6.11 | β | 1H | d | 15 |
| 6.72 | γ | 1H | dd | 11, 15 |
| 7.25 | δ | 1H | dd | 11, 15 |

EXAMPLE 4

Figure 5:
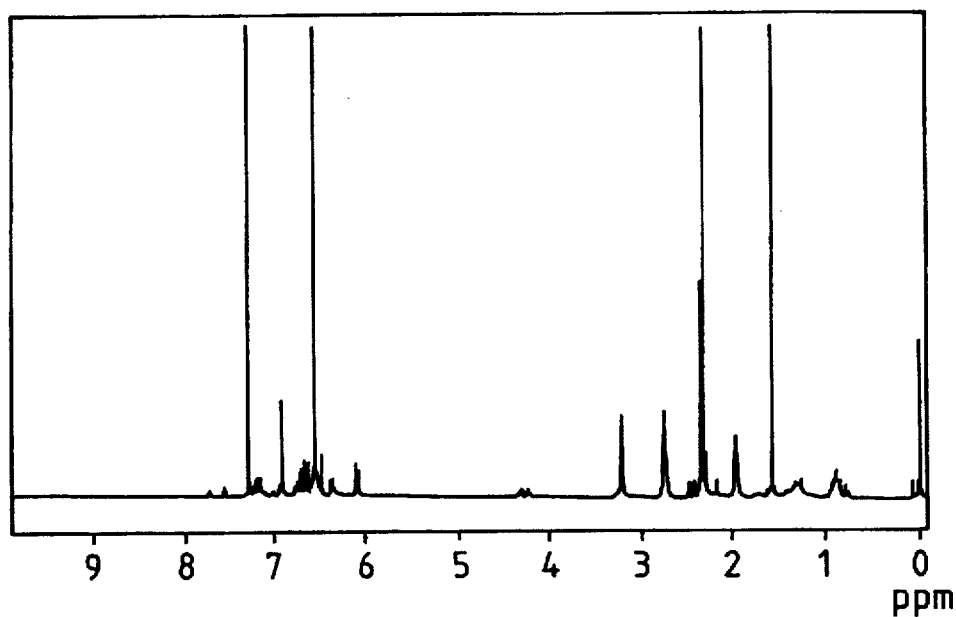
FIG. 5 shows a $^1$H-NMR spectrum of a compound obtained in Example 4.
Figure 6:
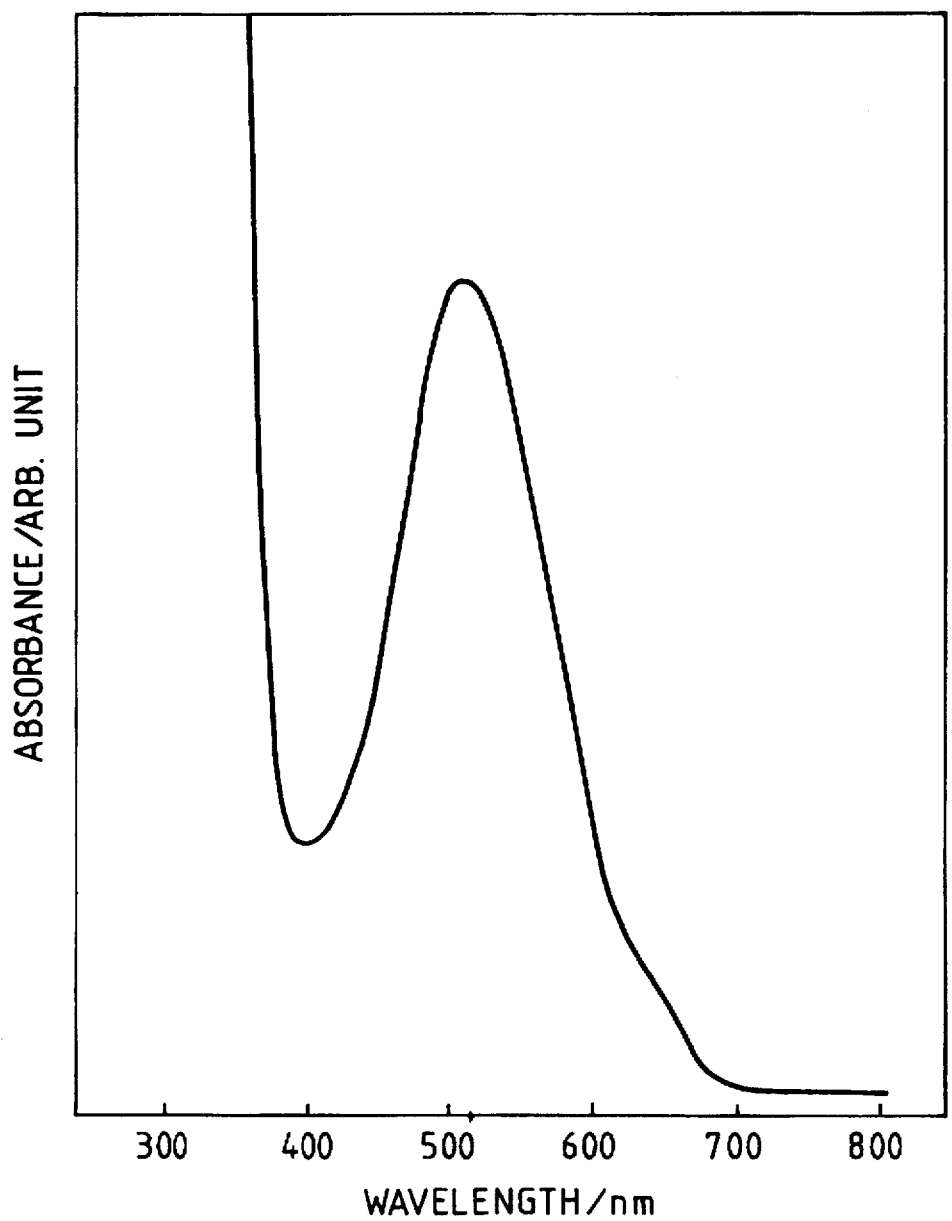
FIG. 6 shows a visible light absorption spectrum of a THF solution of a compound obtained in Example 4.

The same procedure as in Example 1 was carried out to obtain the following dye (pyran-J-D3). The obtained compound was identified by $^1$H-NMR, and a spectrum shown in FIG. 5 was obtained, and therefrom the results in Table 4 were obtained. In consequence, it was confirmed that the obtained compound had the following structure. Furthermore, an absorption spectrum of a THF solution of the obtained dye shown in FIG. 6 was obtained.

For comparison, the absorption spectrum of pyran-J-D3 was standardized and superposed upon that of the THF solution of pyran-J-D2, as shown in FIG. 2. As a result, it is apparent that the absorption spectrum of pyran-J-D3 of this example is shifted to longer wavelength side than the spectrum of pyran-J-D2 in Example 2.

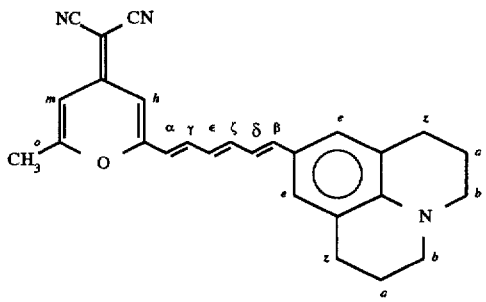

TABLE 4

Measured Results of NMR (pyran-J-D3)

| Chemical Shift (ppm) | Position | Integral Ratio | Multi-plicity | J Value (Hz) |
|---|---|---|---|---|
| 2.73 | z | 4H | t | 6 |
| 2.00 | a | 4H | m | 6 |
| 3.20 | b | 4H | t | 6 |
| 6.90 | e | 2H | s | |
| 6.47 | h | 1H | s | |
| 6.52 | m | 1H | s | |
| 2.32 | o | 3H | s | |
| 6.59 | α | 1H | d | 15 |
| 6.07 | β | 1H | d | 15 |
| 6.65 | γ | 1H | dd | 10, 14 |
| 7.17 | δ | 1H | dd | 11, 15 |
| 6.73 | ε | 1H | dd | 10, 14 |
| 6.35 | ζ | 1H | dd | 10, 14 |

EXAMPLE 5

Figure 7:
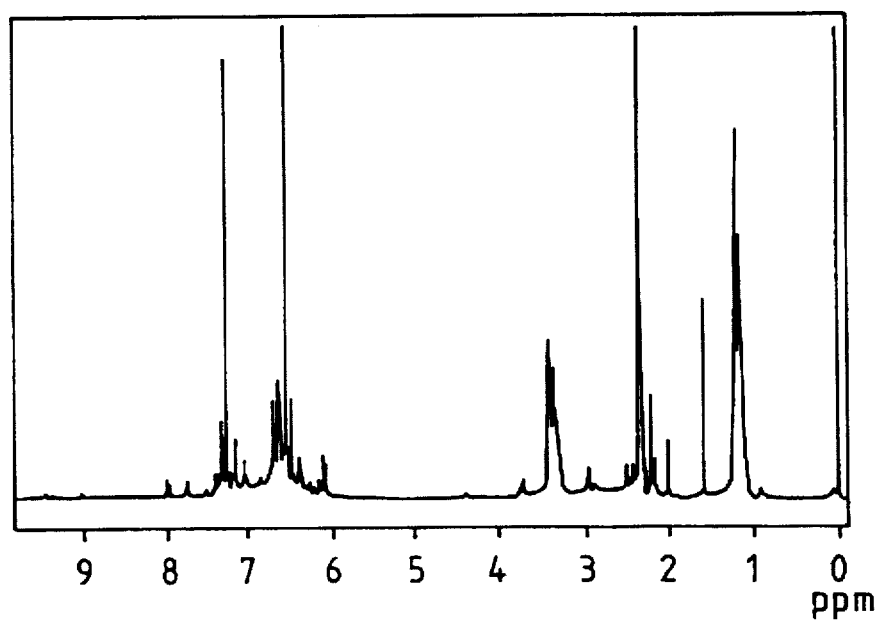
FIG. 7 shows a $^1$H-NMR spectrum of a compound obtained in Example 5.
Figure 8:
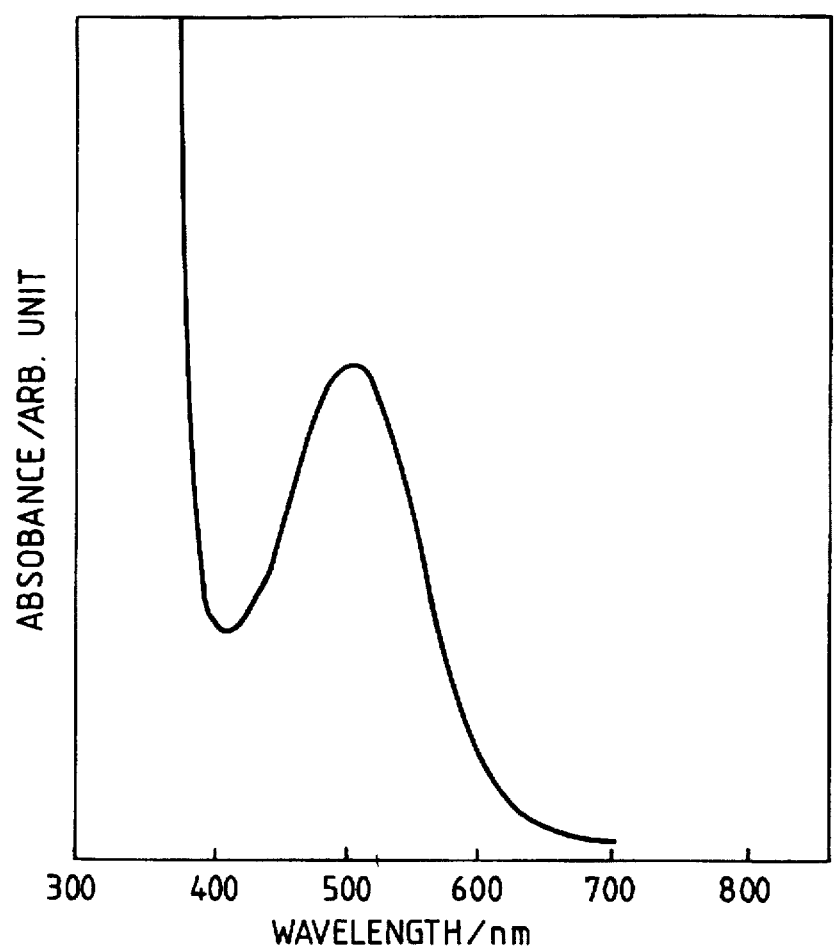
FIG. 8 shows a visible light absorption spectrum of a THF solution of a compound obtained in Example 5.

The same procedure as in Example 1 was carried out to obtain the following dye (pyran-E-D3). The obtained compound was identified by $^1$H-NMR, and a spectrum shown in FIG. 7 was realized, and therefrom the results in Table 5 were obtained. In consequence, it was confirmed that the obtained compound had the following structure. Furthermore, an absorption spectrum of a THF solution of the obtained dye shown in FIG. 8 was run.

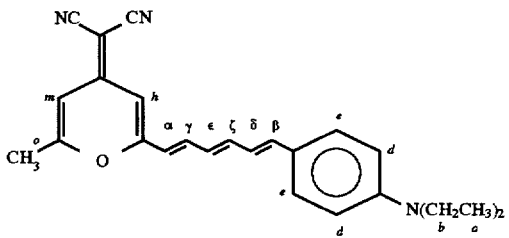

TABLE 5

Measured Results of NMR (pyran-E-D3)

| Chemical Shift (ppm) | Position | Integral Ratio | Multi-plicity | J Value (Hz) |
|---|---|---|---|---|
| 1.19 | a | 6H | t | 7 |
| 3.39 | b | 4H | q | 7 |
| 6.97 | d, e | 4H | dd | 9 |
| 6.48 | h | 1H | s | |

TABLE 5-continued

Measured Results of NMR (pyran-E-D3)

| Chemical Shift (ppm) | Position | Integral Ratio | Multi-plicity | J Value (Hz) |
|---|---|---|---|---|
| 6.53 | m | 1H | s | |
| 2.32 | o | 3H | s | |
| 6.60 | α | 1H | d | 14 |
| 6.04 | β | 1H | d | 15 |
| 6.63 | γ | 1H | dd | 10, 14 |
| 7.18 | δ | 1H | dd | 11, 15 |
| 6.72 | ε | 1H | dd | 10, 15 |
| 6.38 | ζ | 1H | dd | 11, 14 |

TABLE 6

Measured Results of NMR (pyran-E-D4)

| Chemical Shift (ppm) | Position | Integral Ratio | Multi-plicity | J Value (Hz) |
|---|---|---|---|---|
| 1.17 | a | 6H | t | 7 |
| 3.37 | b | 4H | q | 7 |
| 6.95 | d, e | 2H | dd | 9 |
| 6.49 | h | 1H | s | |
| 6.54 | m | 1H | s | |
| 2.32 | o | 3H | s | |
| 6.58 | α | 1H | d | 15 |
| 6.09 | β | 1H | d | 15 |
| 6.68 | γ | 1H | dd | 11, 14 |
| 7.15 | δ | 1H | dd | 11, 15 |
| 6.68 | ε | 1H | dd | 11, 14 |
| 6.35 | ζ | 1H | dd | 11, 15 |
| 6.68 | η | 1H | dd | 10, 15 |
| 6.67 | θ | 1H | dd | 12, 14 |

EXAMPLE 6

Figure 9:
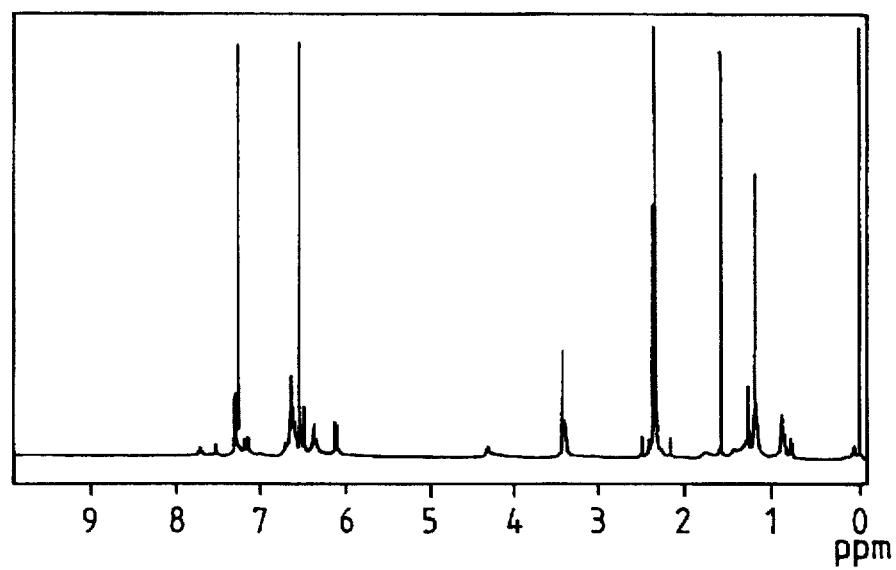
FIG. 9 shows a $^1$H-NMR spectrum of a compound obtained in Example 6.
Figure 10:
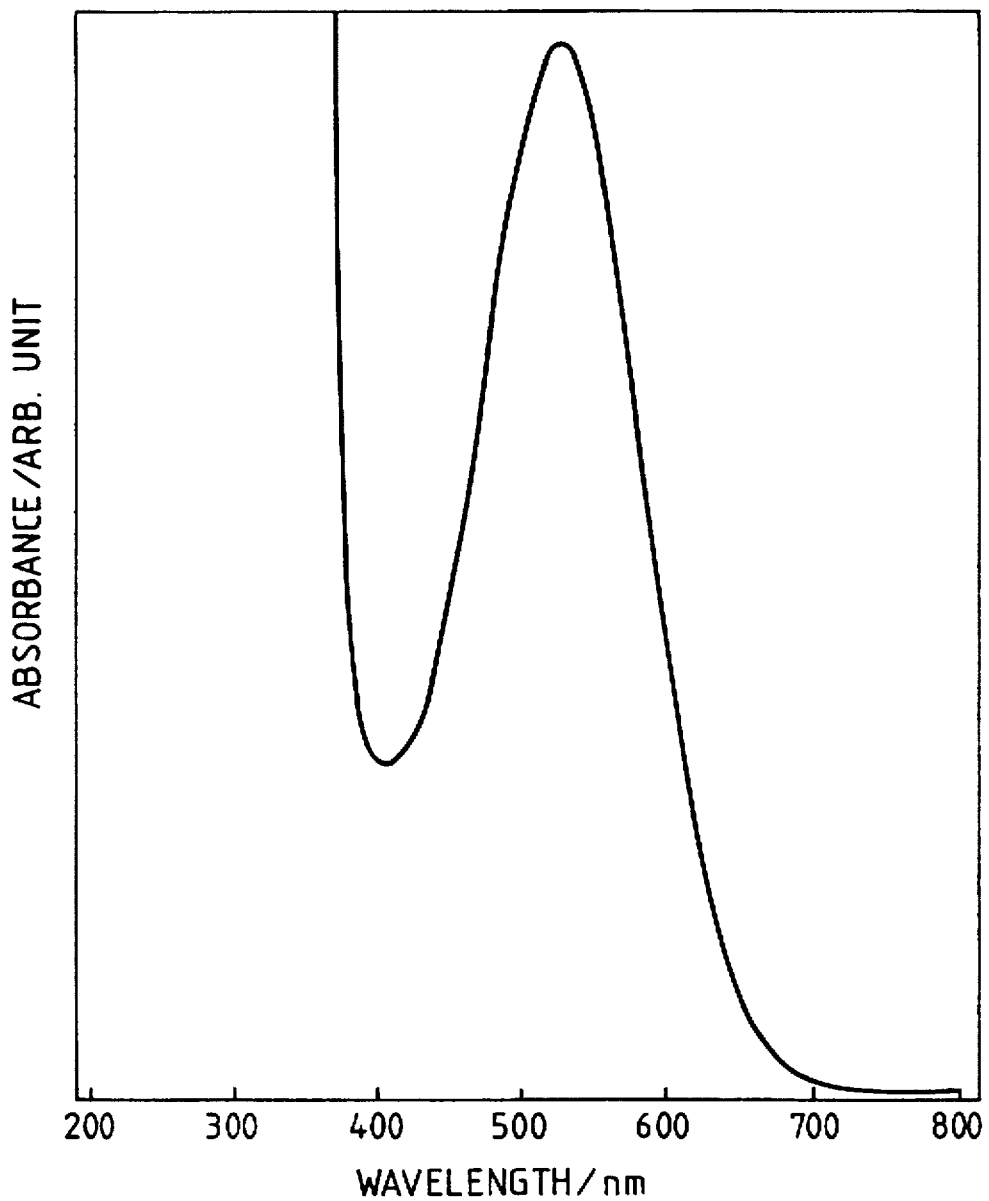
FIG. 10 shows a visible light absorption spectrum of a THF solution of a compound obtained in Example 6.

The same procedure as in Example 1 was carried out to obtain the following dye (pyran-E-D4). The obtained compound was identified by $^1$H-NMR, and a spectrum shown in FIG. 9 was obtained, and therefrom the results in Table 6 were obtained. In consequence, it was confirmed that the obtained compound had the following structure. Furthermore, an absorption spectrum of a THF solution of the obtained dye is shown in FIG. 10.

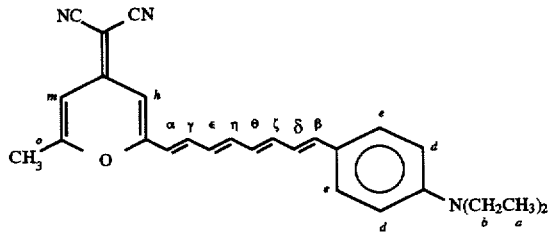

EXAMPLE 7

0.01 g pyran-J-D1 obtained in Example 1, 3.0 g styrene and 0.10 g bis(t-butylphenyl)iodonium hexafluorophosphate were dissolved in 50 cm$^3$ benzene to obtain a photosensitive resin composition of the present invention.

Next, this photosensitive solution was sealed up in a glass ampule, and it was then exposed for 1 minute to a metal halide lamp (SMR 150, made by Toshiba Litek Co., Ltd.) equipped with a filter for cutting off light having wavelengths of 450 nm or less. This reaction solution was poured into methanol to precipitate the resulting polymer.

The obtained polymer had a weight average molecular weight (Mw) of 105,000.

EXAMPLES 8 TO 13

The same procedure as in Example 7 was carried out except that the following conditions were used, to prepare photosensitive resin compositions of the present invention, and polymers were then synthesized in the same manner as in Example 7. In each example, the weight average molecular weight (Mw) of the obtained polymer was measured.

Table 7 shows the reaction conditions of the respective examples and the measured results of the weight average molecular weight of the obtained polymer.

TABLE 7

Reaction Conditions in Examples 8 to 13 and Measured Results of Weight Average Molecular Weight

| Example No. | Dye-stuff | Initiator | Monomer | Wavelength (nm) | Mw |
|---|---|---|---|---|---|
| 8 | Pyran-J-D3 | (t-Bu—⟨Ph⟩—)$_2$I$^+$ PF$_6^-$ | 1,5-pentane-diol acrylate | 550 or more | 15,000 |
| 9 | Pyran-E-D2 | [Ph-N-N-N-N-Ph structure with Ph groups] | Methyl methacrylate | 500 or more | 12,000 |

TABLE 7-continued

Reaction Conditions in Examples 8 to 13 and
Measured Results of Weight Average Molecular Weight

| Example No. | Dyestuff | Initiator | Monomer | Wavelength (nm) | Mw |
|---|---|---|---|---|---|
| 10 | Pyran-E-D1 | (structure with (CH₃)₃COOC groups on benzene ring) | Styrene | 450 or more | 240,000 |
| 11 | Pyran-J-D2 | (Ph-substituted N-containing structure) | (CH₃, O, (CH₂)₄ structure) | 500 or more | 24,000 |
| 12 | Pyran-E-D3 | CHI₃ | N-vinylcarbazole | 550 or more | 105,000 |
| 13 | Pyran-E-D2 | t-Bu—(phenyl)—I⁺ BF₄⁻ | p-bromostyrene | 500 or more | 740,000 |

EXAMPLE 14

4 g poly(methyl methacrylate/methacrylic acid) (a 90/10 mol ratio) was further added to a photosensitive solution of a photosensitive resin composition before polymerization in Example 8, and a glass substrate was then coated with the mixture, followed by drying, to obtain a hologram recording medium of the present invention.

On this hologram recording medium, a line image was depicted with light from an Ar laser (wavelength=488 nm, beam diameter=1 mm) (by the use of a rotary mirror), and then washed with isopropyl alcohol/water (10/90) to obtain a resin line image.

EXAMPLE 15

4 g polymethacrylate/polymethyl methacrylate (20/80) was further added to a photosensitive solution of a photosensitive resin composition before polymerization in Example 9, and a glass substrate was then coated with the mixture, followed by drying, to obtain a hologram recording medium of the present invention.

On this hologram recording medium, a line image was depicted with light from an Ar laser (wavelength=488 nm, beam diameter=1 mm) (by the use of a rotary mirror), and then washed with an aqueous alkaline isopropyl alcohol solution to obtain a resin line image.

EXAMPLE 16

4 g poly(styrene-MMA) was further added to a photosensitive solution of a photosensitive resin composition before polymerization in Example 10, and a glass substrate was then coated with the mixture, followed by drying, to obtain a hologram recording medium of the present invention.

On this hologram recording medium, a line image was formed with light from an Ar laser (wavelength=488 nm, beam diameter=1 mm) (by the use of a rotary mirror), and then washed with cold chloroform to obtain a resin line image.

EXAMPLES 17 AND 18

The same procedure as in Example 7 was carried out except that the following conditions were used and a monomer in Example 7 was replaced with a crosslinkable polymer, to obtain crosslinkable photosensitive resin compositions of the present invention, and crosslinked products were then obtained in the same manner as in Example 7. For these products, weight-average molecular weight was measured, and the results are set forth in Table 8.

TABLE 8

Reaction Conditions in Examples 17 and 18 and Weight Average Molecular Weight of Crosslinked Product

| Example | Sensitizer | Crosslinking Agent | Polymer | Cut Wavelength (nm) | Crosslinked Product (Mw) |
|---|---|---|---|---|---|
| 17 | Pyran-J-D1 | 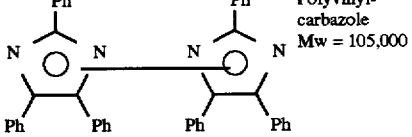 | Polyvinylcarbazole Mw = 105,000 | 500 or less | 950,000 |
| 18 | Pyran-E-D2 | CHI$_3$ | Poly(p-chlorostyrene) Mw = 120,000 | 550 or less | 1,500,000 |

EXAMPLE 19

0.01 g pyran-J-D1 obtained in Example 1, 5.0 g polyvinylcarbazole, 0.5 g bis(t-butylphenyl)iodonium hexafluorophosphate and 0.1 g iodoform were dissolved in 60 cm$^1$ toluene to obtain a photosensitive resin composition of the present invention. Next, a glass substrate was spin-coated with this photosensitive solution to obtain a 15-μm-thick hologram recording medium of the present invention.

The obtained hologram recording medium was exposed to an argon laser light of 488 nm at an exposure of 100 mJ/cm$^2$, and then developed with xylene and hexane to obtain a reflective type volume phase hologram.

A diffraction efficiency of the obtained volume phase hologram was about 75%.

EXAMPLES 20 TO 23

The same procedure as in Example 19 was carried out except that the following conditions were used, to prepare volume phase holograms, and a diffraction efficiency of each hologram was then measured.

The conditions in the respective examples and the results of the diffraction efficiency are shown in Table 9.

TABLE 9

Reaction Conditions in Examples 20 to 24 and Deffraction Efficiency of Product

| Example No. | Sensitizer | Amount of Sensitizer (g) | Exposure Wavelength (nm) | Crosslinking Agent | Amount of Crosslinking Agent (g) | Diffraction Efficiency (%) |
|---|---|---|---|---|---|---|
| 24 | Pyran-E-D2 | 0.007 | 514.5 | 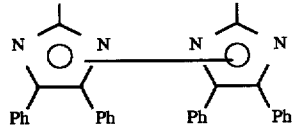 | 0.1 | 71 |
| 25 | Pyran-J-D2 | 0.01 | 514.5 | 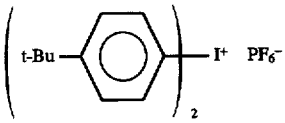 | 0.15 | 70 |
| 26 | Pyran-E-D3 | 0.01 | 632.8 | CHI$_3$ | 0.2 | 52 |
| 27 | Pyran-J-D3 | 0.008 | 632.8 | 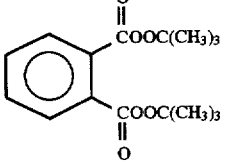 | 0.07 | 56 |

As described above, a pyran derivative of the present invention can shift an absorption maximum to a longer wavelength side, and so it has a high absorption sensitivity to light having a wavelength of 514.5 nm from an Ar laser and even to light having a long wavelength of about 600 nm or more from an He—Ne laser and shows an excellent photosensitivity.

Furthermore, this pyran derivative and a specific pyran derivative can be used as sensitizers to provide an excellent photosensitive resin composition and a hologram recording medium mainly comprising the composition.

What is claimed is:

1. A pyran derivative having a structure represented by the following formula (1)

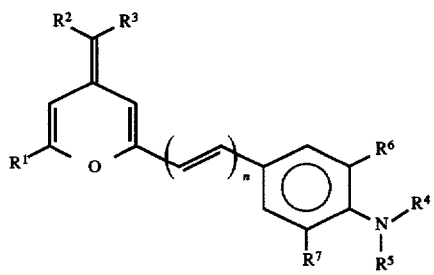

wherein n is 3 or 4; $R^1$ is a proton, an alkyl group having 1 to 4 carbon atoms or a substituted or unsubstituted phenyl group; each of $R^2$ and $R^3$ is independently a cyano group, an alkoxycarbonyl group having an alkyl moiety of 1 to 4 carbon atoms, an acyl group having an alkyl moiety of 1 to 4 carbon atoms, an aracyl group having a substitute or unsubstituted phenyl group, a sulfonyl group which is unsubstituted or substituted by an alkyl group having 1 to 4 carbon atoms, a substituted or unsubstituted aryl group, or a substituted or unsubstituted aryloxy group; each of $R^4$ and $R^5$ is an alkyl group having 1 to 6 carbon atoms; and each of $R^6$ and $R^7$ is a proton, provided that $R^4$ and $R^5$ are alkyl groups, and a pair of $R^4$ and $R^6$ as well as a pair of $R^5$ and $R^7$ can be bonded to each other to form a five-membered heterocyclic ring, a six-membered heterocyclic ring or a seven-membered heterocyclic ring.

2. The pyran derivative according to claim 1 which is represented by the formula (2) or (3):

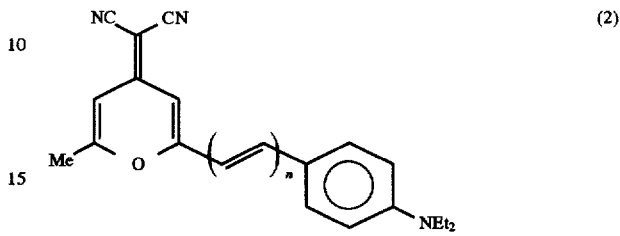

wherein n = 3 or 4

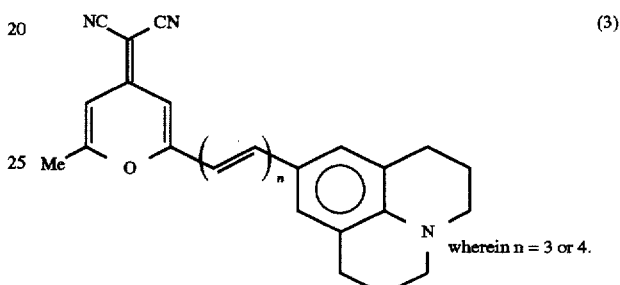

wherein n = 3 or 4.

* * * * *